(12) United States Patent
Jacobs

(10) Patent No.: US 11,478,320 B2
(45) Date of Patent: Oct. 25, 2022

(54) MEDICAL DEVICE HOLDER

(71) Applicant: Jacobs Emerging Technologies, LLC, Bloomfield Hills, MI (US)

(72) Inventor: Michael John Jacobs, Bloomfield Hills, MI (US)

(73) Assignee: Jacobs Emerging Technologies, LLC, Bloomfield Hills, MI (US)

( * ) Notice: Subject to any disclaimer, the term of this patent is extended or adjusted under 35 U.S.C. 154(b) by 288 days.

(21) Appl. No.: 15/750,276

(22) PCT Filed: Sep. 22, 2015

(86) PCT No.: PCT/US2015/051455
§ 371 (c)(1),
(2) Date: Feb. 5, 2018

(87) PCT Pub. No.: WO2017/023338
PCT Pub. Date: Feb. 9, 2017

(65) Prior Publication Data
US 2018/0214230 A1  Aug. 2, 2018

Related U.S. Application Data

(60) Provisional application No. 62/201,761, filed on Aug. 6, 2015.

(51) Int. Cl.
*A61B 50/20* (2016.01)
*A61B 46/23* (2016.01)
(Continued)

(52) U.S. Cl.
CPC .............. *A61B 50/20* (2016.02); *A61B 46/23* (2016.02); *A61B 50/00* (2016.02); *A61B 90/50* (2016.02); *A61B 2050/3008* (2016.02)

(58) Field of Classification Search
CPC ......... A61B 50/20; A61B 50/30; A61B 50/33; A61B 2050/3008; A61B 2050/314;
(Continued)

(56) References Cited

U.S. PATENT DOCUMENTS 825,774 A * 7/1906 Stumm .................... A47K 1/09
   211/119.009
1,790,085 A * 1/1931 Barringer ............... A45D 44/18
   206/209.1
(Continued)

FOREIGN PATENT DOCUMENTS

DE         2339724 A1 *  2/1975  .......... A61M 25/002

OTHER PUBLICATIONS

International Search Report for PCT/US2015/051455, ISA/US, dated Dec. 17, 2015.
(Continued)

*Primary Examiner* — Jonathan Liu
*Assistant Examiner* — Taylor L Morris
(74) *Attorney, Agent, or Firm* — Harness, Dickey & Pierce, P.L.C.

(57) ABSTRACT

The medical device holder can be attached to a plurality of different support structures to retain a medical device at a convenient location near a patient. The medical device holder includes an elongated housing which defines a pair of storage areas for a medical device. The housing is formed of a first planar member fixed to a second concave member. The concave member defines first and second chambers, the first being generally L-shaped.

21 Claims, 21 Drawing Sheets

(51) Int. Cl.
    *A61B 50/00*      (2016.01)
    *A61B 90/50*      (2016.01)
    *A61B 50/30*      (2016.01)

(58) Field of Classification Search
    CPC ......... A61B 46/00; A61B 46/23; A61B 90/53; A61B 2050/005; A61B 2050/0084; A61B 2050/0083; A61B 2050/0082; A61B 50/00; A61B 90/50; A61L 2/26; A61L 2202/24; A61L 2202/182; A61G 15/16; B65D 73/0064; B65D 2251/1033; B65D 75/366; B65D 75/367; A46B 17/04; A47F 7/0021; A47F 7/0028; A47K 1/09; A61C 15/043
    USPC .............. 248/314, 311.2, 111, 309.1
    See application file for complete search history.

(56) References Cited

U.S. PATENT DOCUMENTS

| | | | | |
|---|---|---|---|---|
| 2,544,856 A * | 3/1951 | Perlin | A47K 1/09 | 206/362 |
| 2,572,697 A * | 10/1951 | Buckner | A47K 1/09 | 312/207 |
| 3,166,189 A * | 1/1965 | Disston | A61M 25/002 | 206/364 |
| 3,494,458 A * | 2/1970 | Meierhoefer | B65D 55/024 | 206/366 |
| 3,604,616 A * | 9/1971 | Greif | B65D 75/30 | 206/439 |
| 3,746,162 A * | 7/1973 | Bridges | A46B 17/04 | 206/361 |
| 4,005,776 A * | 2/1977 | Seeley | B65D 75/366 | 206/306 |
| 4,153,160 A * | 5/1979 | Leigh | A61B 50/33 | 206/370 |
| 4,190,166 A * | 2/1980 | Allsop | A47F 7/0028 | 211/162 |
| 4,193,496 A * | 3/1980 | Barratt | B65D 43/162 | 206/380 |
| 4,260,057 A * | 4/1981 | Wall-Andersen | B65D 85/20 | 206/379 |
| 4,366,901 A * | 1/1983 | Short | A61J 1/2096 | 206/210 |
| 4,423,811 A * | 1/1984 | Knapp | B65D 43/162 | 206/15.3 |
| 4,436,700 A * | 3/1984 | Erickson | B01L 9/543 | 206/443 |
| 4,444,332 A * | 4/1984 | Widen | B65D 43/0212 | 215/321 |
| 4,519,501 A * | 5/1985 | Gerwin | A61B 50/30 | 206/204 |
| 4,597,493 A * | 7/1986 | Bruso | B65D 73/0021 | 206/363 |
| 4,619,364 A * | 10/1986 | Czopor, Jr. | B25H 3/003 | 206/379 |
| 4,746,008 A * | 5/1988 | Heverly | B65D 55/02 | 206/1.5 |
| 4,774,063 A * | 9/1988 | Runnells | A61L 2/26 | 220/324 |
| 4,798,292 A * | 1/1989 | Hauze | A61L 2/26 | 206/439 |
| 4,807,747 A * | 2/1989 | Hadtke | B65D 25/105 | 206/327 |
| 4,886,165 A * | 12/1989 | Annett | A61B 50/31 | 206/370 |
| 4,925,448 A * | 5/1990 | Bazaral | A61M 25/002 | 206/364 |
| 4,930,638 A * | 6/1990 | Vasconcellos | A45D 44/18 | 206/362.2 |
| 4,979,616 A * | 12/1990 | Clanton | A61M 5/3205 | 206/364 |
| 5,031,768 A * | 7/1991 | Fischer | A61B 50/31 | 206/364 |
| 5,036,866 A * | 8/1991 | Eldrige, Jr. | A61B 46/23 | 128/849 |
| 5,076,437 A * | 12/1991 | Schindler | A45C 11/20 | 206/508 |
| 5,095,924 A * | 3/1992 | Stanfield | A45D 44/18 | 206/581 |
| 5,133,454 A * | 7/1992 | Hammer | A61M 5/002 | 206/364 |
| 5,165,540 A * | 11/1992 | Forney | A61M 25/002 | 206/363 |
| 5,178,267 A * | 1/1993 | Grabenkort | A61B 5/1495 | 206/210 |
| 5,211,915 A * | 5/1993 | Monch | A61L 2/26 | 422/547 |
| 5,224,679 A * | 7/1993 | Code | A61G 13/10 | 128/852 |
| 5,246,022 A * | 9/1993 | Israel | A61C 15/043 | 132/324 |
| 5,293,993 A * | 3/1994 | Yates, Jr. | A61M 5/3205 | 206/365 |
| 5,311,990 A * | 5/1994 | Kalinski | B65D 25/04 | 206/370 |
| 5,360,110 A * | 11/1994 | Hirai | B65D 73/02 | 206/464 |
| 5,372,787 A * | 12/1994 | Ritter | A61L 2/26 | 206/363 |
| 5,388,741 A * | 2/1995 | Hillinger | G01B 3/1071 | 224/679 |
| 5,392,917 A * | 2/1995 | Alpern | B65D 77/2056 | 206/370 |
| 5,407,070 A * | 4/1995 | Bascos | A61M 5/002 | 206/364 |
| 5,411,193 A * | 5/1995 | Culp | A45F 5/02 | 206/366 |
| 5,441,152 A * | 8/1995 | Estes | B25H 3/006 | 206/349 |
| D370,174 S * | 5/1996 | Bergstedt | D9/415 | |
| D370,626 S * | 6/1996 | Pass | D15/140 | |
| 5,531,341 A * | 7/1996 | Shlisky | A61M 5/3205 | 206/366 |
| 5,533,618 A | 7/1996 | Pickels, Jr. | | |
| 5,540,901 A * | 7/1996 | Riley | A61L 2/26 | 422/300 |
| 5,549,204 A * | 8/1996 | Toren | A61J 1/035 | 206/469 |
| 5,549,388 A * | 8/1996 | Wilkes | B65D 33/20 | 206/438 |
| 5,566,828 A * | 10/1996 | Claes | A61M 5/003 | 206/570 |
| 5,570,856 A * | 11/1996 | Sharpe | B65D 25/107 | 206/485 |
| 5,584,408 A * | 12/1996 | Orkisz | B65D 43/162 | 220/4.22 |
| 5,638,951 A * | 6/1997 | Fukura | G01J 5/02 | 206/306 |
| 5,645,167 A * | 7/1997 | Conrad | B44D 3/125 | 206/1.5 |
| 5,709,221 A | 1/1998 | Vancaillie et al. | | |
| 5,752,286 A * | 5/1998 | Wright | B08B 3/04 | 134/169 R |
| 5,759,502 A * | 6/1998 | Spencer | A61L 2/26 | 206/370 |
| 5,772,031 A * | 6/1998 | Landis | A61B 50/30 | 206/363 |
| 5,775,511 A * | 7/1998 | Stark | B65D 75/367 | 206/45.24 |
| 5,779,046 A * | 7/1998 | Plakos | A46B 17/04 | 206/362.3 |
| 5,816,401 A * | 10/1998 | Vasudeva | B25H 3/003 | 206/377 |
| 5,832,543 A * | 11/1998 | Bosserman | A61J 19/00 | 4/259 |
| 5,842,567 A * | 12/1998 | Rowe | A61B 50/3001 | 206/464 |

(56) References Cited

U.S. PATENT DOCUMENTS

| | | | | |
|---|---|---|---|---|
| 5,924,567 A * | 7/1999 | Wenum | A46B 17/04 | 206/15.3 |
| 5,960,801 A * | 10/1999 | Vermooten | A46B 17/04 | 132/286 |
| 5,966,902 A * | 10/1999 | Korycki | B65D 75/22 | 206/209 |
| 6,021,901 A * | 2/2000 | Wolfe | B65D 43/162 | 206/1.5 |
| 6,077,074 A * | 6/2000 | Homra | A61M 1/0039 | 433/77 |
| 6,084,211 A * | 7/2000 | Bauer | B26B 29/04 | 219/222 |
| 6,155,439 A * | 12/2000 | Draughn | A61B 50/22 | 211/85.13 |
| 6,196,410 B1 * | 3/2001 | Hocking | B44D 3/126 | 206/209 |
| 6,237,772 B1 * | 5/2001 | LaMarche | B65D 21/0202 | 206/470 |
| 6,241,092 B1 * | 6/2001 | Vasudeva | B65D 25/103 | 206/349 |
| 6,253,773 B1 * | 7/2001 | Ingemann | A47K 1/09 | 132/308 |
| 6,308,875 B1 | 10/2001 | Almo | | |
| 6,364,182 B1 * | 4/2002 | Hansen | B26B 5/002 | 206/359 |
| 6,367,110 B1 * | 4/2002 | Urueta | A61B 18/1402 | 15/160 |
| 6,391,260 B1 * | 5/2002 | Davis | A61L 2/14 | 206/370 |
| 6,436,085 B1 * | 8/2002 | Lauer | A61M 39/10 | 604/408 |
| 6,534,000 B1 * | 3/2003 | Michaelson | A61C 19/002 | 206/363 |
| 6,575,298 B1 * | 6/2003 | McArthur | A61B 50/20 | 206/363 |
| 6,585,942 B1 * | 7/2003 | Bussell | A61L 2/26 | 206/349 |
| 6,594,971 B1 * | 7/2003 | Addy | B65D 75/30 | 53/413 |
| 6,666,348 B2 * | 12/2003 | Fore | B65D 1/26 | 220/315 |
| 6,766,906 B2 * | 7/2004 | Charng | B65D 43/162 | 206/461 |
| 6,827,212 B2 * | 12/2004 | Reaux | A61B 17/06161 | 206/372 |
| 6,832,686 B2 * | 12/2004 | Donegan | B65D 77/02 | 206/1.5 |
| 6,871,767 B2 * | 3/2005 | Perlman | B43K 23/04 | 206/214 |
| 6,896,141 B2 * | 5/2005 | McMichael | A61B 50/30 | 206/370 |
| 6,910,581 B2 * | 6/2005 | McMichael | A61B 50/30 | 206/370 |
| 7,036,454 B2 * | 5/2006 | Davis | A01K 1/0613 | 119/417 |
| 7,147,129 B1 * | 12/2006 | Menefield | A61F 6/005 | 221/283 |
| 7,316,318 B1 * | 1/2008 | Rosten | B65D 81/075 | 206/363 |
| 7,331,462 B2 * | 2/2008 | Steppe | A61B 50/30 | 206/370 |
| 7,348,572 B2 * | 3/2008 | Shin | A61L 2/10 | 250/455.11 |
| 7,360,650 B2 * | 4/2008 | Hoffecker | A45D 44/18 | 132/309 |
| 7,377,780 B2 * | 5/2008 | White | A61C 19/00 | 433/77 |
| 7,401,703 B2 * | 7/2008 | McMichael | A61B 50/33 | 206/370 |
| 7,422,106 B1 * | 9/2008 | Kendra | A61F 15/003 | 206/204 |
| 7,422,431 B2 * | 9/2008 | White | A61C 19/00 | 433/77 |
| 7,565,972 B2 * | 7/2009 | Steppe | A61L 2/26 | 206/370 |
| 7,637,218 B1 * | 12/2009 | Burton | A45C 9/00 | 108/43 |
| 7,694,814 B1 * | 4/2010 | Cristobal | A61B 8/4422 | 206/438 |
| 7,913,959 B2 * | 3/2011 | White | A61C 19/00 | 248/314 |
| 8,038,025 B2 * | 10/2011 | Stark | A61B 50/362 | 220/254.3 |
| 8,104,614 B2 * | 1/2012 | Pinal | A61B 50/00 | 206/370 |
| 8,226,669 B2 * | 7/2012 | Detruit | A61F 2/0095 | 606/151 |
| 8,245,857 B2 * | 8/2012 | DiGasbarro | A61G 7/0503 | 211/85.13 |
| 8,267,246 B2 * | 9/2012 | Bettenhausen | A61B 50/34 | 206/363 |
| 8,453,977 B2 * | 6/2013 | Zoland | A61B 50/13 | 248/37.6 |
| 8,685,068 B2 * | 4/2014 | Sixto | A61B 17/8014 | 606/286 |
| 9,072,543 B2 * | 7/2015 | Miller | A61B 50/20 | |
| 9,265,578 B2 * | 2/2016 | Dacey | A61B 50/33 | |
| 9,364,288 B2 * | 6/2016 | Smith | A61B 50/20 | |
| 9,414,893 B2 * | 8/2016 | Jacobson | B65B 5/04 | |
| 9,603,690 B1 * | 3/2017 | Lho | A61C 19/02 | |
| 9,708,101 B2 * | 7/2017 | Kinskey | B65D 25/04 | |
| 9,872,754 B2 * | 1/2018 | Tuechsen | A61F 2/0095 | |
| 10,384,033 B2 * | 8/2019 | Gustavsson | A61M 25/0017 | |
| 10,532,864 B2 * | 1/2020 | Austin | B65D 43/164 | |
| 10,894,441 B2 * | 1/2021 | Treacy | B44D 3/123 | |
| 2002/0040912 A1 * | 4/2002 | McHugh | A61B 50/20 | 221/45 |
| 2003/0234206 A1 * | 12/2003 | Hetzler | A46B 15/0091 | 206/581 |
| 2004/0108236 A1 * | 6/2004 | Reed | B44D 3/04 | 206/361 |
| 2004/0195131 A1 * | 10/2004 | Spolidoro | A61B 50/33 | 206/438 |
| 2005/0019237 A1 * | 1/2005 | Riley | A61L 2/26 | 422/297 |
| 2005/0194507 A1 * | 9/2005 | White | A61B 50/36 | 248/314 |
| 2005/0230280 A1 * | 10/2005 | Sotiropolous | A61B 90/50 | 206/363 |
| 2006/0181181 A1 * | 8/2006 | Calfee | A46B 17/04 | 312/206 |
| 2006/0243635 A1 * | 11/2006 | Sullivan | A61B 17/3217 | 206/571 |
| 2006/0273084 A1 * | 12/2006 | Baker | A61L 2/26 | 220/23.4 |
| 2007/0246471 A1 * | 10/2007 | Hrovat | A61J 7/0069 | 220/533 |
| 2008/0296447 A1 * | 12/2008 | Peterson | A61B 50/33 | 248/171 |
| 2009/0301927 A1 * | 12/2009 | Fvlbrook | A61B 90/57 | 248/304 |
| 2010/0065456 A1 * | 3/2010 | Junk | A61L 2/26 | 206/363 |
| 2010/0308055 A1 * | 12/2010 | Sams | A61M 5/3205 | 220/324 |
| 2011/0084039 A1 * | 4/2011 | Walters | A47F 7/0028 | 211/85.13 |
| 2011/0174318 A1 * | 7/2011 | Reyes | A61B 46/00 | 128/852 |
| 2011/0295239 A1 * | 12/2011 | Gustavsson | A61M 25/0111 | 604/544 |
| 2012/0028212 A1 * | 2/2012 | Fujii | A61C 5/44 | 433/72 |
| 2012/0037526 A1 * | 2/2012 | Mulone | A61M 5/002 | 206/366 |
| 2013/0213843 A1 * | 8/2013 | Knight | A61L 2/26 | 206/438 |

(56) References Cited

U.S. PATENT DOCUMENTS

| | | | |
|---|---|---|---|
| 2013/0220855 A1* | 8/2013 | Markovitch | A61L 2/26 206/363 |
| 2013/0327663 A1* | 12/2013 | Telford | A61B 46/23 206/363 |
| 2014/0048431 A1* | 2/2014 | Young | A61L 2/00 206/363 |
| 2014/0077435 A1* | 3/2014 | Powell | A61L 2/26 269/308 |
| 2014/0202918 A1* | 7/2014 | Huxford | A61M 15/009 206/570 |
| 2014/0242542 A1* | 8/2014 | Jubenville | A61C 19/00 433/79 |
| 2014/0251845 A1* | 9/2014 | Roesler | B65D 77/02 206/363 |
| 2015/0101616 A1* | 4/2015 | Wiley | A61B 50/20 128/852 |
| 2015/0144515 A1* | 5/2015 | Chartres | B65D 55/022 206/370 |
| 2015/0151017 A1* | 6/2015 | Tipton | A61L 2/26 422/310 |
| 2015/0182686 A1* | 7/2015 | Okihara | A61B 50/30 206/366 |
| 2016/0058511 A1* | 3/2016 | Starnes | A61B 90/08 206/570 |
| 2016/0074118 A1* | 3/2016 | Tuechsen | A61F 2/0095 206/572 |
| 2016/0213441 A1* | 7/2016 | Connolly | A61B 50/33 |
| 2016/0228676 A1* | 8/2016 | Glithero | G09B 19/00 |
| 2017/0144807 A1* | 5/2017 | Rud | B65D 43/20 |
| 2017/0290634 A1* | 10/2017 | Dacey | B65D 65/22 |
| 2018/0029785 A1* | 2/2018 | Mitten | B65D 85/20 |
| 2018/0084901 A1* | 3/2018 | Lamothe | A46B 17/04 |
| 2018/0235348 A1* | 8/2018 | Booker | A45D 42/00 |
| 2018/0296297 A1* | 10/2018 | Moloney | A61B 50/30 |
| 2018/0296298 A1* | 10/2018 | Escobar Fuertes | A61B 50/362 |
| 2018/0318028 A1* | 11/2018 | Spens | A61B 50/30 |
| 2020/0338259 A1* | 10/2020 | Mainz | A61M 5/002 |
| 2021/0069406 A1* | 3/2021 | Politis | A61M 5/3202 |
| 2021/0137629 A1* | 5/2021 | Gunther | A61M 5/002 |

OTHER PUBLICATIONS

Written Opinion of the ISA for PCT/US2015/051455, ISA/US, dated Dec. 17, 2015.

\* cited by examiner

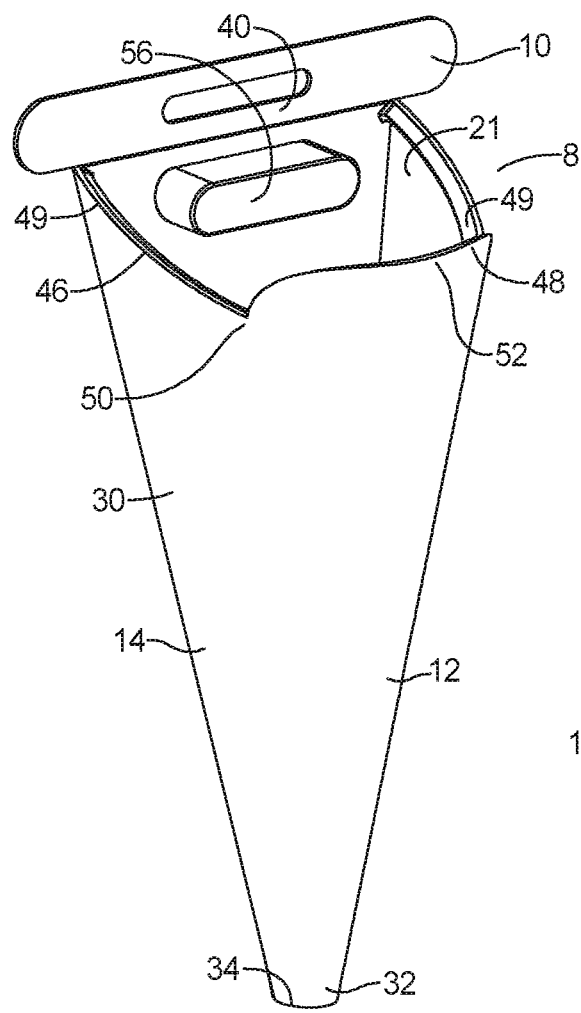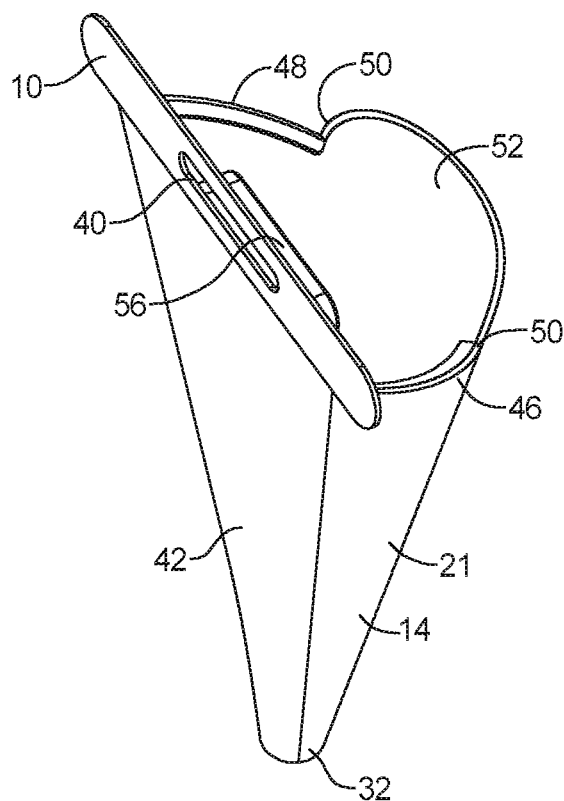
FIG 1
FIG 2

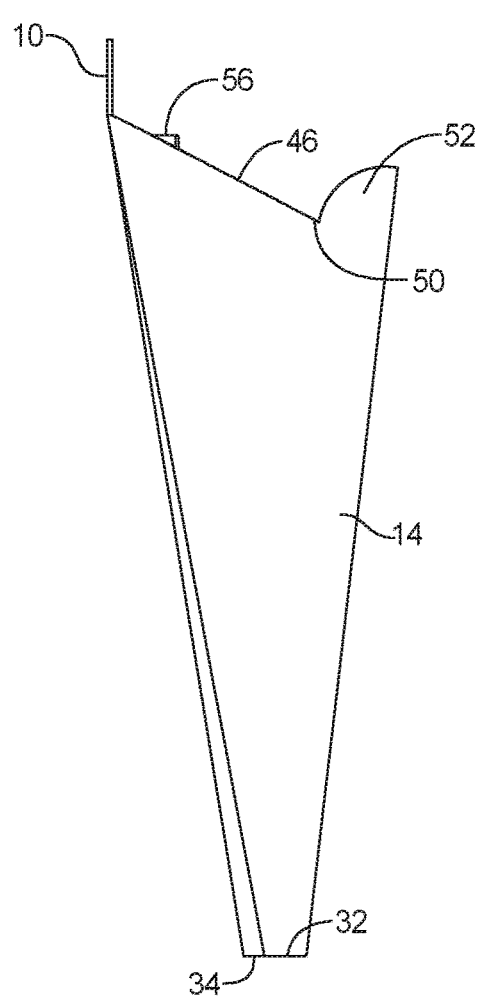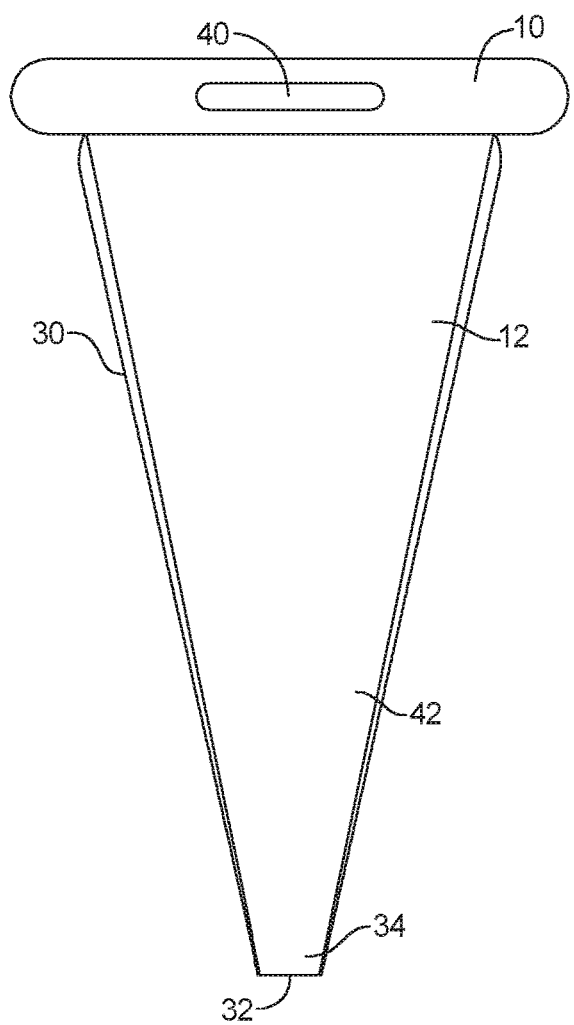

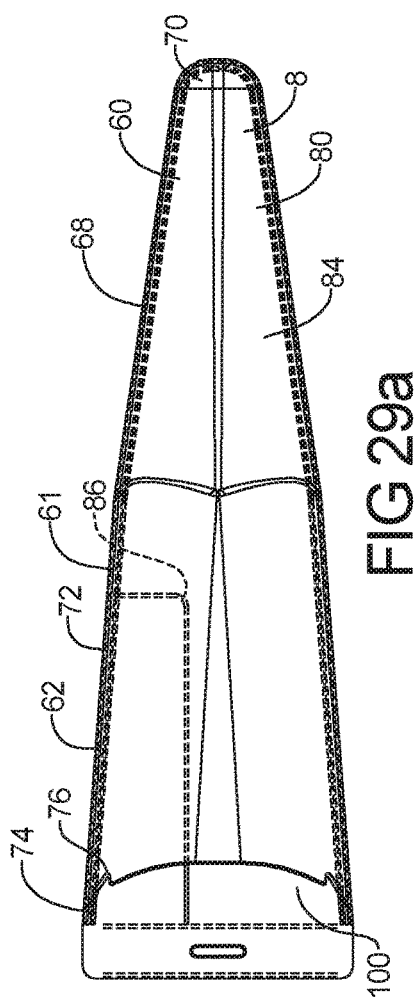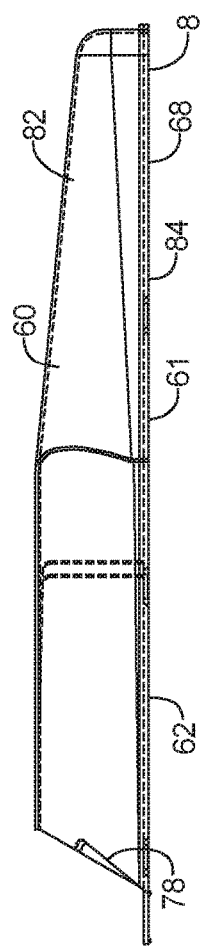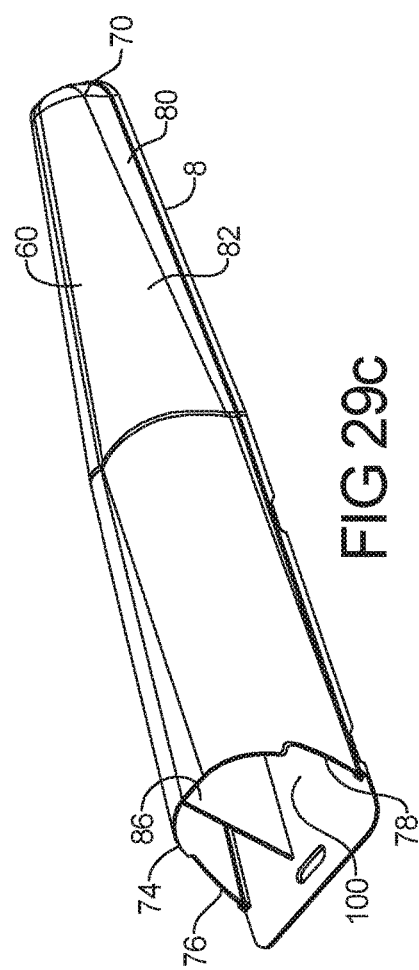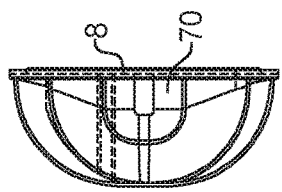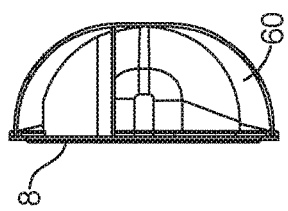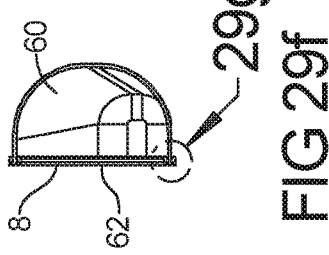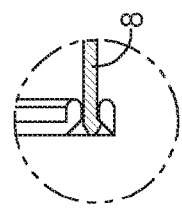

MEDICAL DEVICE HOLDER

CROSS-REFERENCE TO RELATED APPLICATIONS

This application is a 371 U.S. National Stage of International Application No. PCT/US2015/051455, filed Sep. 22, 2015. This application claims the benefit of U.S. Provisional Application No. 62/201,761, filed Aug. 6, 2015. The disclosures of the above applications are incorporated herein by reference.

FIELD

The present invention pertains to the art of medical device holders and, more particularly, to medical device holders that may be utilized at a variety of operating theater locations and offer a selectively engagable integrated disinfection system.

BACKGROUND

This section provides background information related to the present disclosure which is not necessarily prior art. Medical instruments, such as suction devices, scalpels, and thermometers are used to treat patients in and operating theater. Some devices are intended to be used repeatedly on a single patient, and may be used for many hours during a surgical procedure. The rate of replacement of these medical instruments during a procedure is based on functional and infection control considerations that may be unique for each instrument. Among the considerations used to determine the replacement frequency of these instruments is the control of accidental contamination from contact with environmental surfaces. It is well known that exposure to microbes found on environmental surfaces, such as table tops or drapes could adversely affect the health of the patient. Contamination of environmental surfaces from used medical devices can also lead to contamination of subsequent patients if microbes are not removed or killed during the cleaning process. Therefore, it is useful to have a means to store these medical instruments to protect both the patient and others from harm caused by exposure to microbes.

In the absence of appropriate holders, users have been known to store medical instruments in open graduated cylinders and on drapes in the operating theater. These methods encourage accidental contact with potentially contaminated surfaces, as well as allowing the accumulation of secretions from previous uses. In an attempt to address this problem, various storage devices have been developed to store and protect medical instruments. There is a need for a storage device that can be positioned where needed, that can effectively retain a medical instrument in a storage position and that allows for effective infection control practices.

SUMMARY

This section provides a general summary of the disclosure, and is not a comprehensive disclosure of its full scope or all of its features. The present invention is directed to a medical device holder and method for safely storing a medical device.

The medical device holder can be attached to a plurality of different support structures to retain a medical device at a convenient location near a patient. The medical device holder includes an elongated housing which defines a storage area for a medical device. The housing is formed of a first planar member fixed to a second concave member. The concave member defines first and second chambers, the first being generally L-shaped.

Optionally, the housing can include a selectively insertable disinfecting member into the first or second chamber. The disinfecting member can include a UV light source and a battery. The disinfecting member can be elongated so as to position the UV light emitting source at a distal end of the housing.

Additional objects, features and advantages of the present invention will become more readily apparent from the following detailed description of preferred embodiments when taken in conjunction with the drawings wherein like reference numerals refer to corresponding parts in the several views. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1 and 2 represents perspective views of the medical device holder according to the present teachings;

FIGS. 5 and 6 are rear and left side views of the medical device holder shown in FIGS. 1-4;

FIGS. 29a-29g represent views of an alternate medical device holder;

Corresponding reference numerals indicate corresponding parts throughout the several views of the drawings.

DETAILED DESCRIPTION

Figure 3:
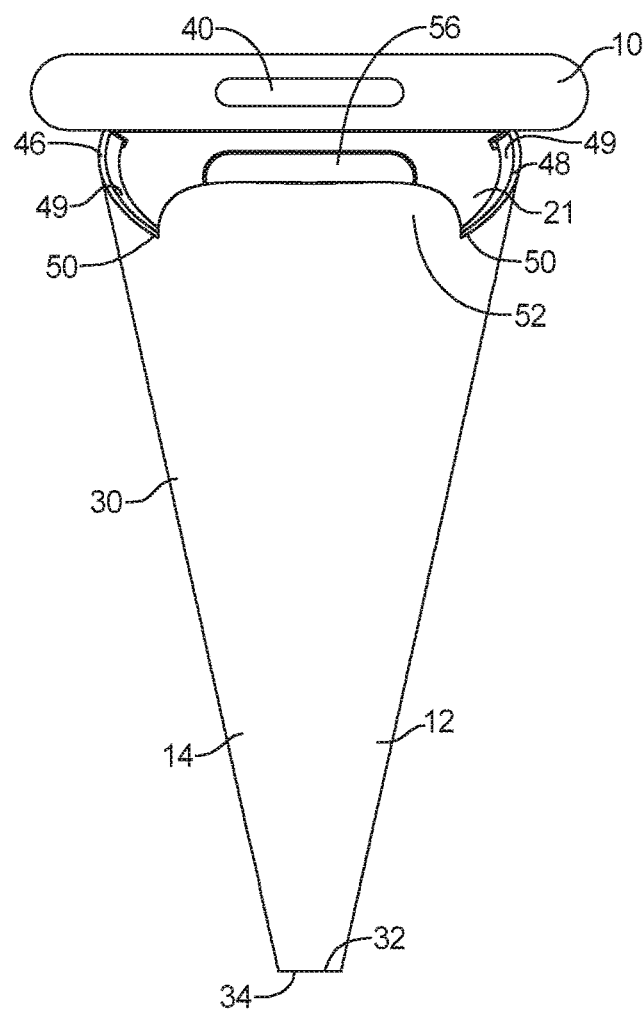
FIGS. 3 and 4 represent front and right side views of the medical device.
Figure 4:
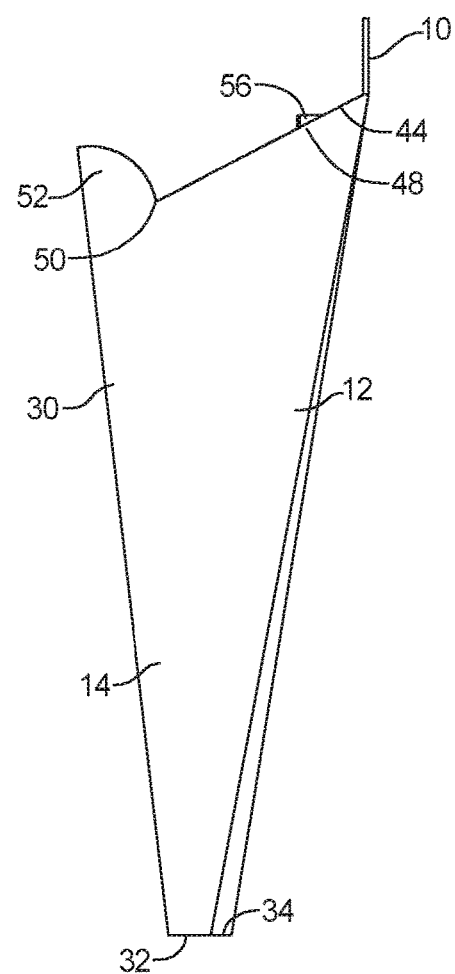
Figure 7:
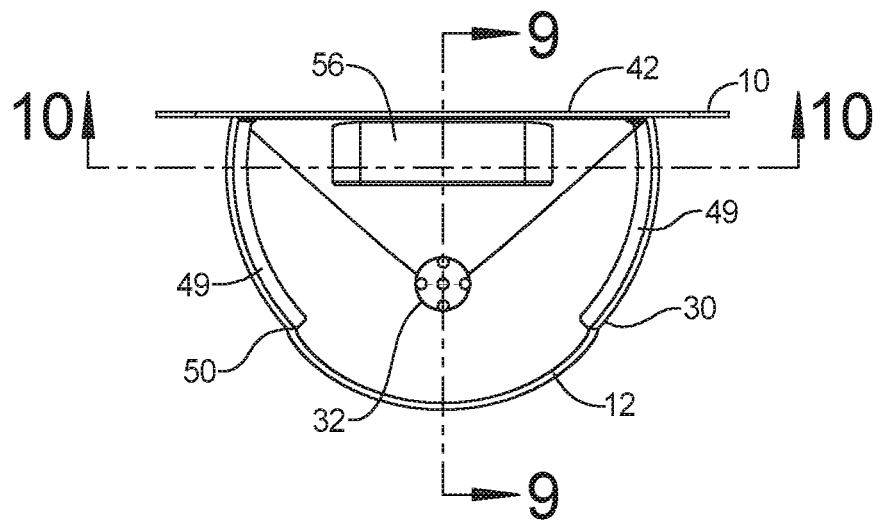
FIGS. 7 and 8 represent top and bottom views of the medical device holder shown in FIGS. 1-6.
Figure 8:
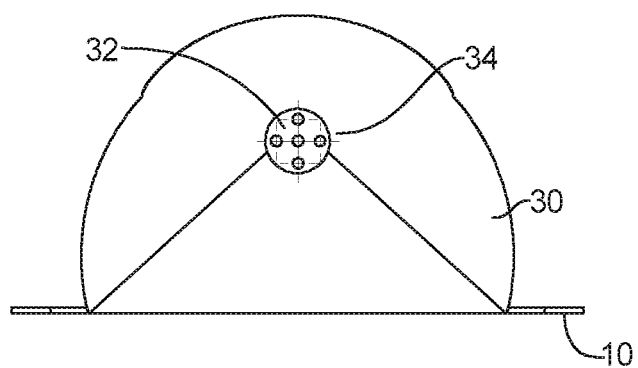
Figure 9:
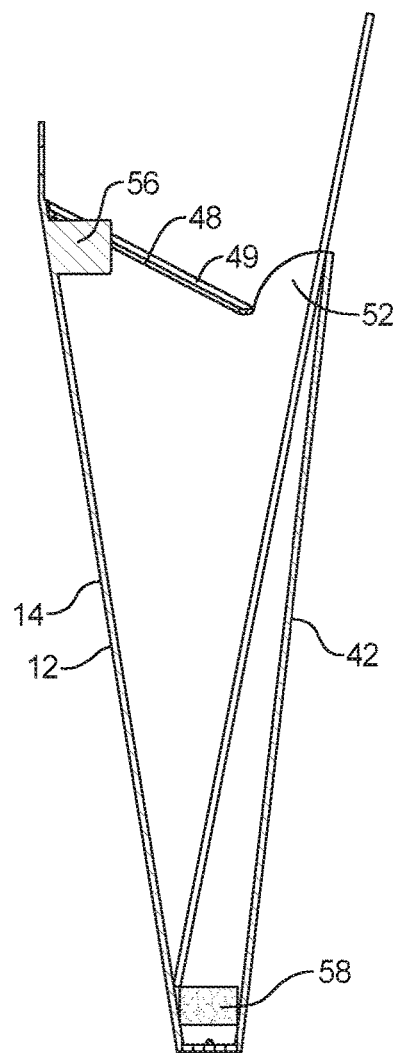
FIGS. 9 and 10 are side and top sectional views of an alternate embodiment.
Figure 10:
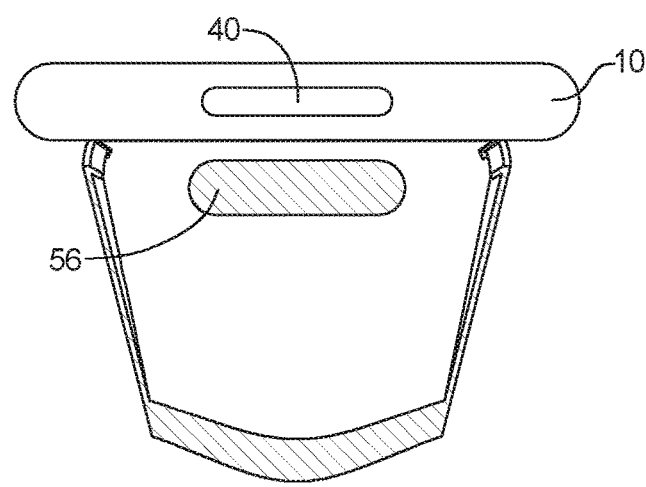
Figure 11:
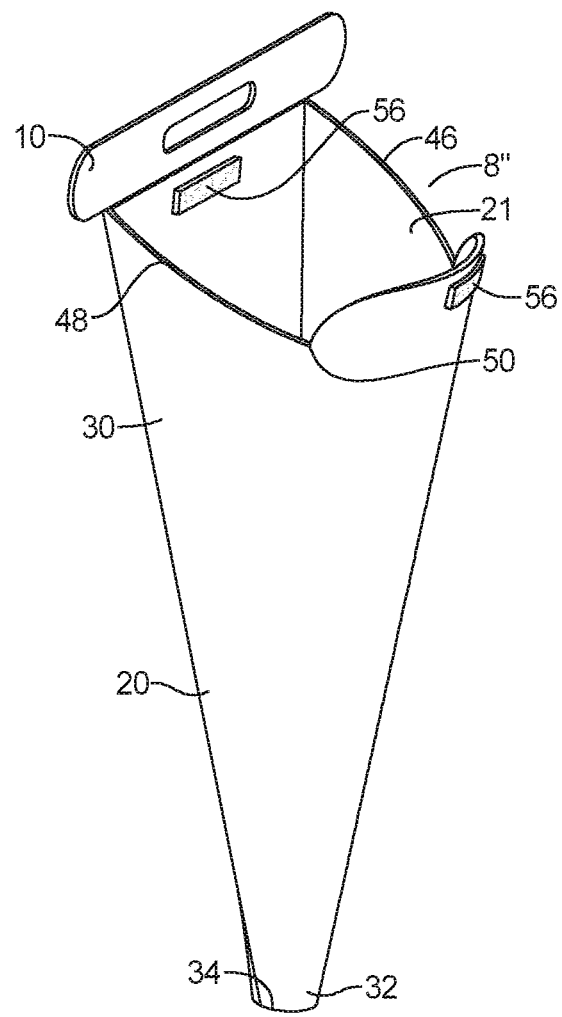
FIGS. 11 and 12 represent perspective views of an alternate medical device holder.

Example embodiments will now be described more fully with reference to the accompanying drawings. With initial reference to FIGS. 1-10, a medical instrument holder assembly 8 is shown including a planar support surface member 10, and a main body 12 of the present invention mounted thereto. The holder assembly 8 includes a main body 12 having at least one sidewall 14 defining an elongated instrument housing 20 having an opening 21 through which a medical instrument (not shown) may be inserted. Preferably, instrument housing 20 is constructed of a semi-rigid plastic. However, housing 20 may alternatively be constructed from fully rigid or flexible materials, or a combination thereof. In this embodiment, main body 12 includes an upper portion 30 that tapers to an end portion 32.

The upper portion 30 and end portion 32 both include generally cylindrical diameters, wherein the diameter of upper portion 30 is larger than the diameter of end portion 32, forming an edge 34 there between. Extending through upper portion 30 is a locking slot or notch 40 which may be utilized to secure the medical device holder to the environment, such as a surgical drape as will be discussed in more detail below.

As shown in FIG. 2, the attachment means is in the form of aperture 40 extending through a middle portion of support surface member 10, which may be utilized to as will be discussed in more detail below. Also shown is the planar back portion 42 that takes the general form of a triangle component that couples to the curved surface of the sidewall 14 of the main body 12. The opening 21 defines a peripheral edge 44 which is segmented in three defined portions, the first and third portions 46 and 48 couple to the flat triangular back portion 42 and define a rib 49 which functions to support the surface an act as a scraping location for the surgical instrument. Coupled to a second end 50 of the first and third portions 46 and 48 is the second protrusion which defines a protruding lip 52, which along with the first and third portions define a scalloped surface which is configures to reduce the tendency of the medical instrument from rotating along the peripheral edge.

As shown in FIGS. 3-10, the medical device holder 8 can include scraping surfaces and structures 49 and 56. These structures can be molded plastic or glued on abrasive materials. Optionally, the end portion 8 and 9, can define holes or apertures that allow the flow out of biological fluids. Optionally, a UV generating source 58 can be disposed within the medical device holding body 12. The UV generating source 58 can be a disk or puck that has a plurality of UV generating sources such as LEDs that are powered. This UV generating source 58 can have a set of batteries are incorporated therein. Optionally, the UV generating source 58 can be is stick member having a handle which is simply dropped into The body 12.

FIGS. 11-19 represent a medical device holder according to an alternate teaching. With initial reference to FIG. 11, a medical instrument holder assembly 8' is shown including a planar support surface member 10, and a main body 12 of the present invention mounted thereto. The holder assembly 8' includes a main body 12 having at least one sidewall 14 defining an elongated instrument housing 20 having an opening 21 through which a medical instrument (not shown) may be inserted. Preferably, instrument housing 20 is constructed of a semi-rigid plastic. However, housing 20 may alternatively be constructed from fully rigid or flexible materials, or a combination thereof. In this embodiment, main body 12 includes an upper portion 30 that tapers to an end portion 32. In this regard, any of the holder 12 can be formed of a rigid inner frame or skeleton which is over molded with a softer material.

The upper portion 30 and end portion 32 both include generally cylindrical diameters, wherein the diameter of upper portion 30 is larger than the diameter of end portion 32, forming an edge 34 there between. Extending through upper portion 30 is a locking slot or notch 40 which may be utilized to secure the medical device holder to the environment, such as a surgical drape as will be discussed in more detail below.

Figure 12:
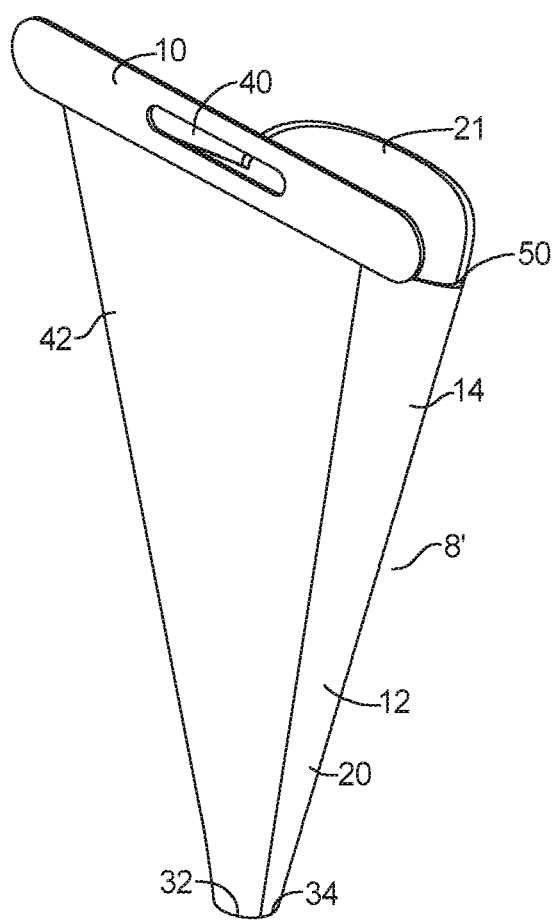
Figure 13:
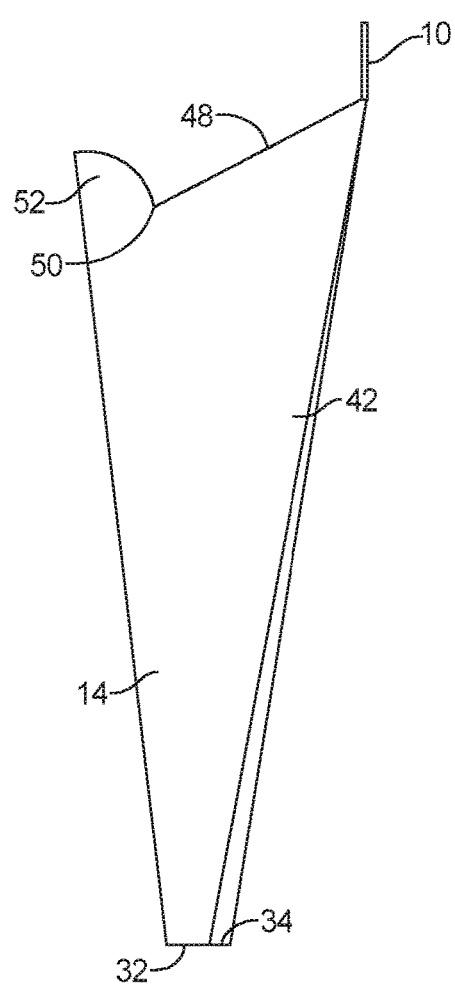
FIGS. 13 and 14 represents right side and front views of the medical device holder shown in FIGS. 11 and 12.
Figure 14:
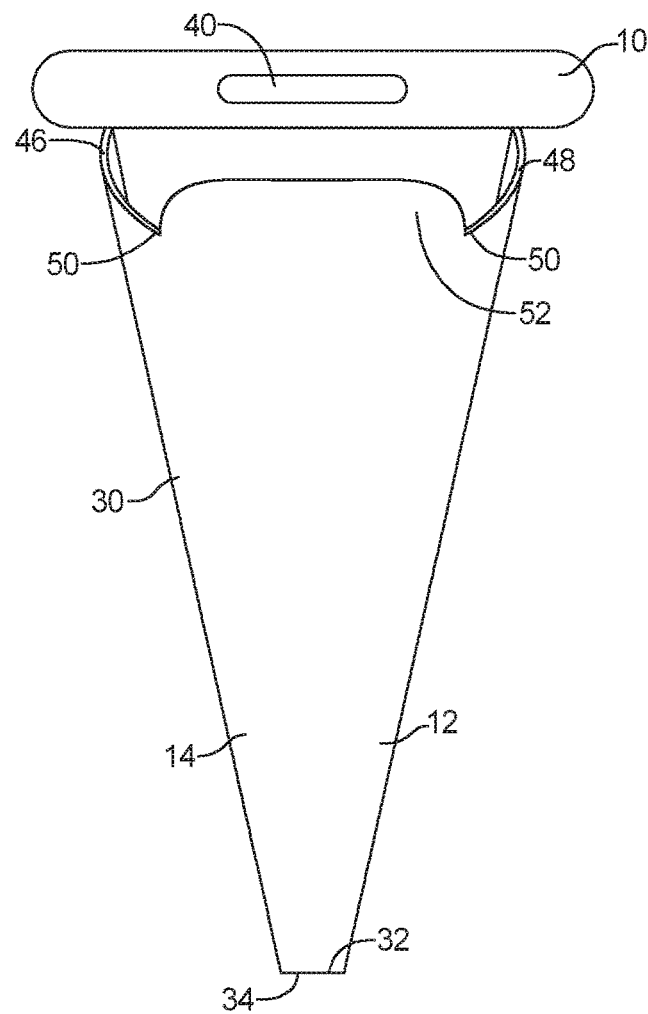
Figure 15:
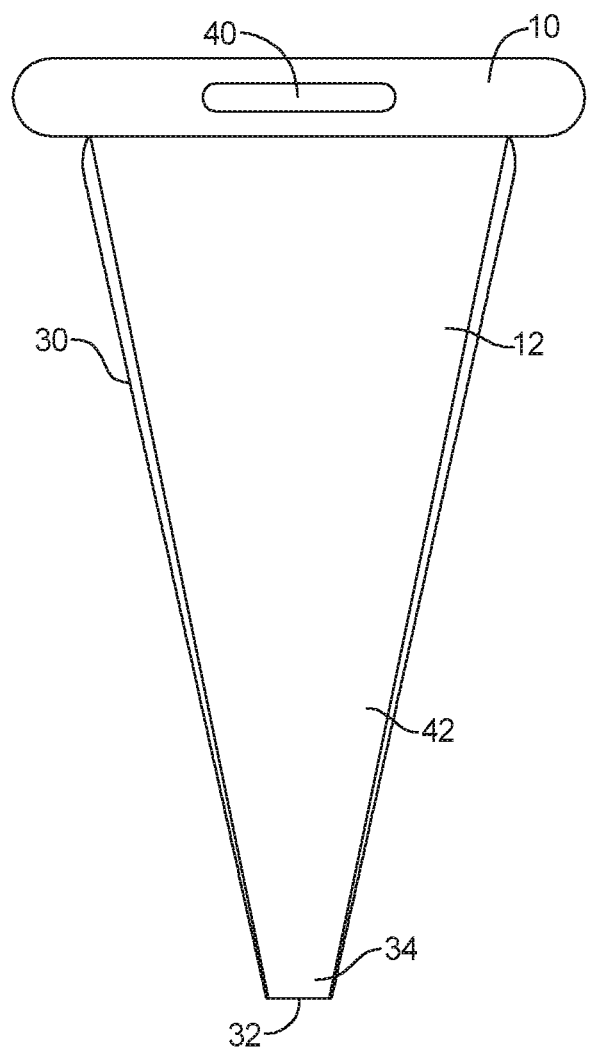
FIGS. 15 and 16 represent rear and left views of the medical device holder shown in FIGS. 13 and 14.
Figure 16:
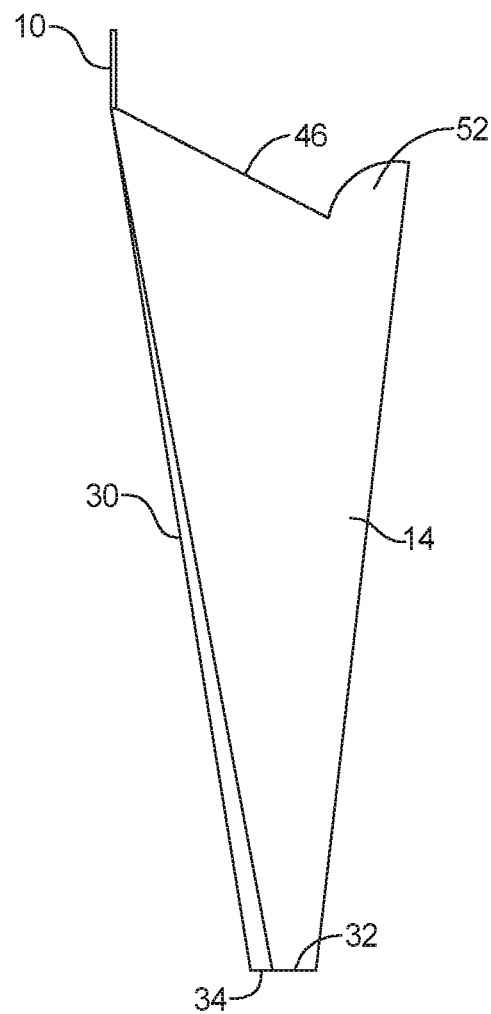
Figure 17:
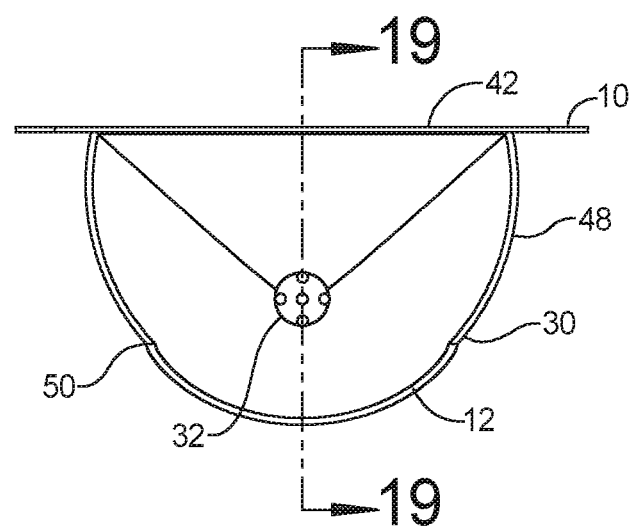
FIGS. 17 and 18 represent top and bottom views of the medical device holder shown in FIGS. 14 and 15.
Figure 18:
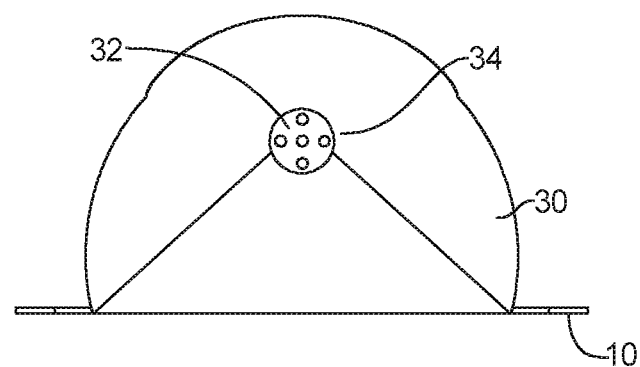
Figure 19:
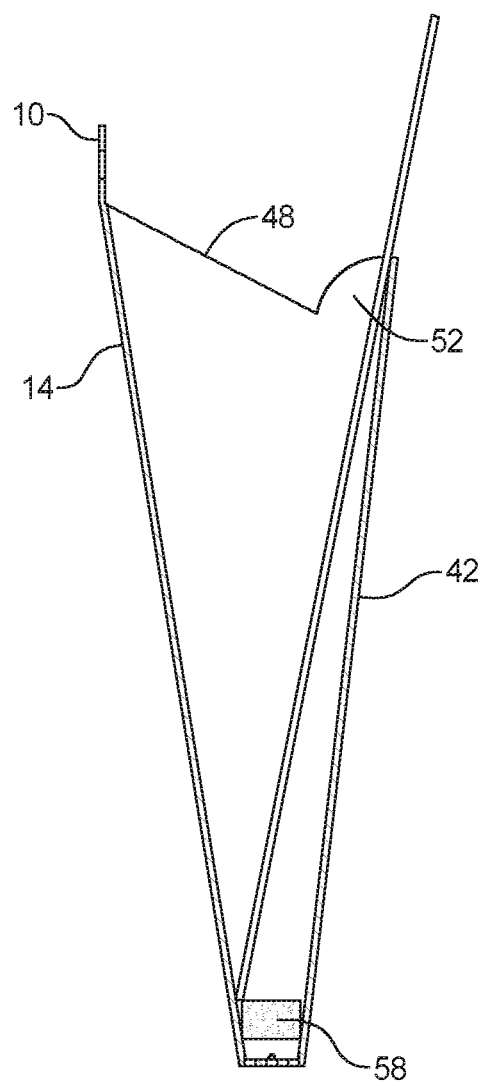
FIG. 19 represents a sectional side view of the medical device holder shown in FIGS. 17 and 18.
Figure 20:
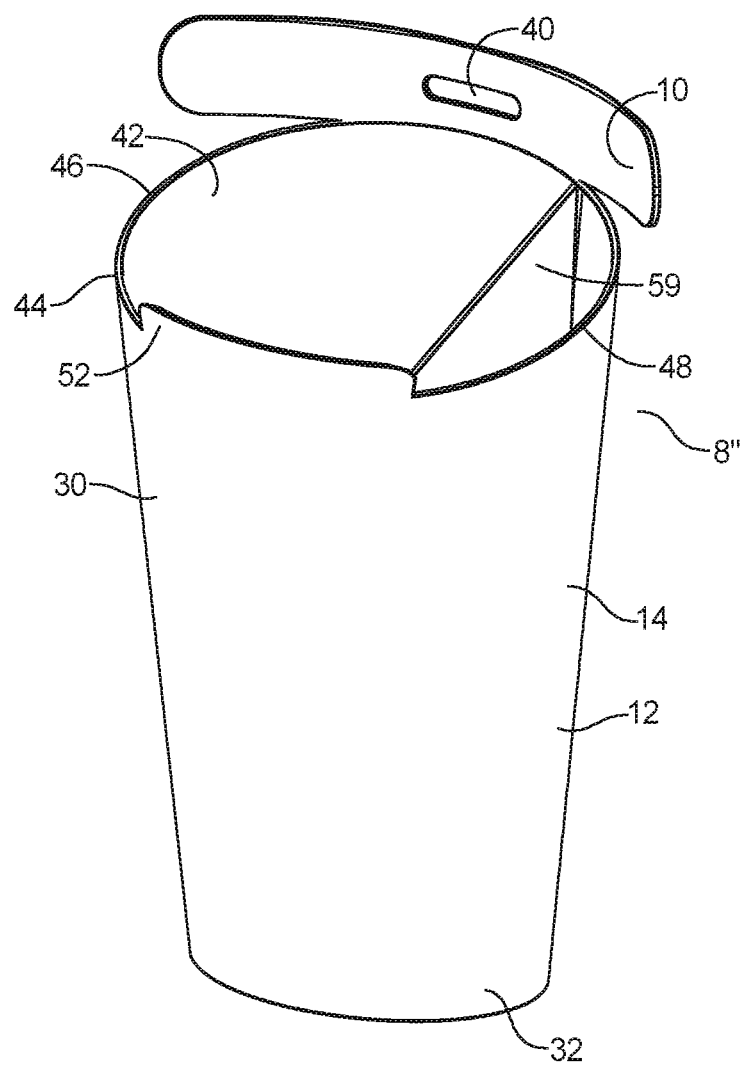
FIG. 20 represents a perspective view of an alternate medical device holder.
Figure 21:
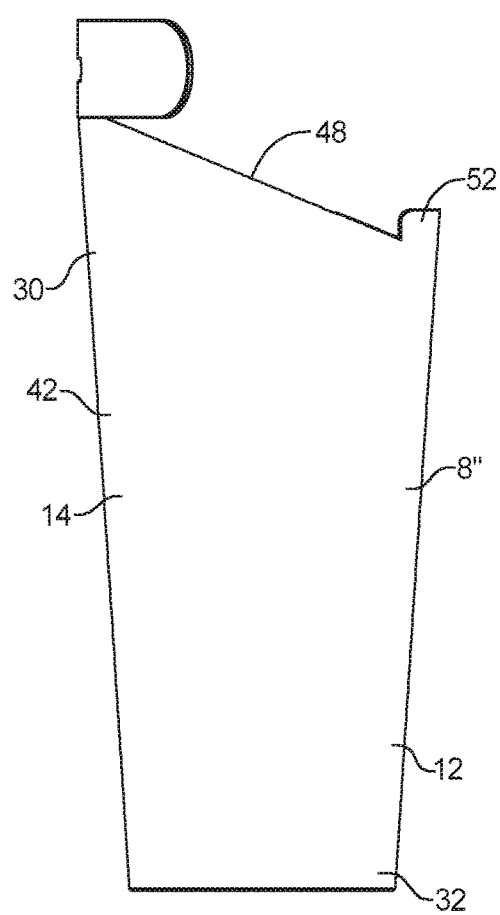
FIGS. 21 and 22 represent front and left side views of the medical device holder shown in FIG. 20.
Figure 22:
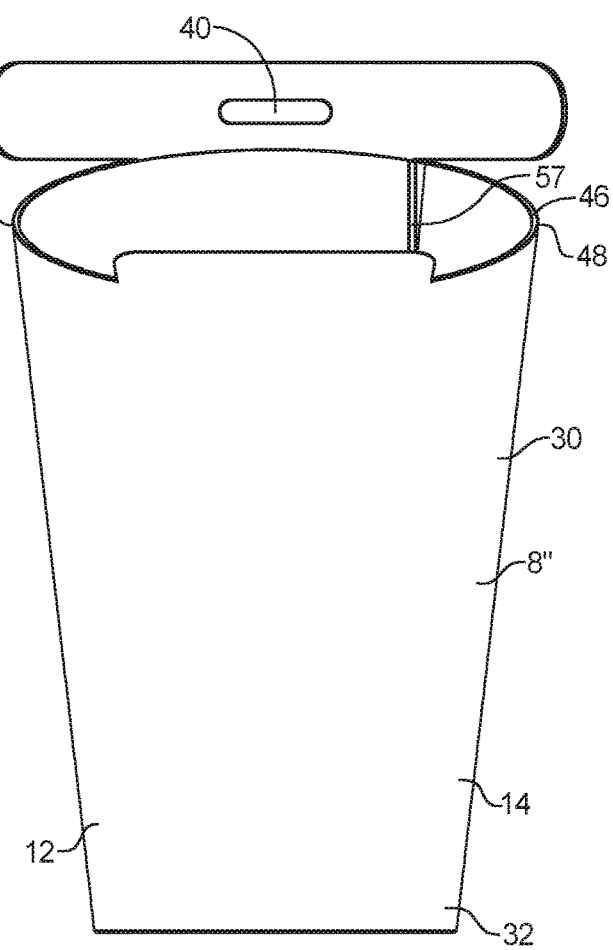

As shown in FIG. 12, the attachment mechanism is in the form of aperture 40 extending through a middle portion of support surface member 10, which may be utilized to as will be discussed in more detail below. Also shown is the planar back portion 42 that takes the general form of a triangle component that couples to the curved surface of the sidewall 14 of the main body 12. The opening 21 defines a peripheral edge 44 that is segmented in three defined portions, the first and third portions 46 and 48 couple to the flat triangular back portion 42. Coupled to a second end 50 of the first and third portions 46 and 48 is the second protrusion which defines a protruding lip 52, which along with the first and third portions define a scalloped surface which is configures to reduce the tendency of the medical instrument from rotating along the peripheral edge.

As shown in FIGS. 13-19, the medical device holder 8 can include scraping surfaces and structures 56 which can be molded or fastened into interior and exterior surfaces. These structures can be molded plastic or glued on abrasive materials. Preferably, the scraping structure can have have a high melting point, which is greater that 212 degrees F. The end portion 32, can define holes or apertures that allow the flow out of biological fluids.

FIGS. 20-28 represent a medical device holder according to an alternate teaching. With initial reference to FIG. 20, a medical instrument holder assembly 8" is shown including a curved support surface member 10, and a main body 12 of the present invention mounted thereto. The holder assembly 8" includes a main body 12 having at least one sidewall 14 defining an elongated instrument housing 20 having an opening 21 through which a medical instrument (not shown) may be inserted. Preferably, instrument housing 20 is constructed of a semi-rigid plastic.

The upper portion 30 and end portion 32 both include generally cylindrical diameters, wherein the diameter of upper portion 30 is larger than the diameter of end portion 32, forming an edge 34 there between. Extending through upper portion 30 is a locking slot or notch 40 which may be utilized to secure the medical device holder to the environment, such as a surgical drape as will be discussed in more detail below.

Figure 23:
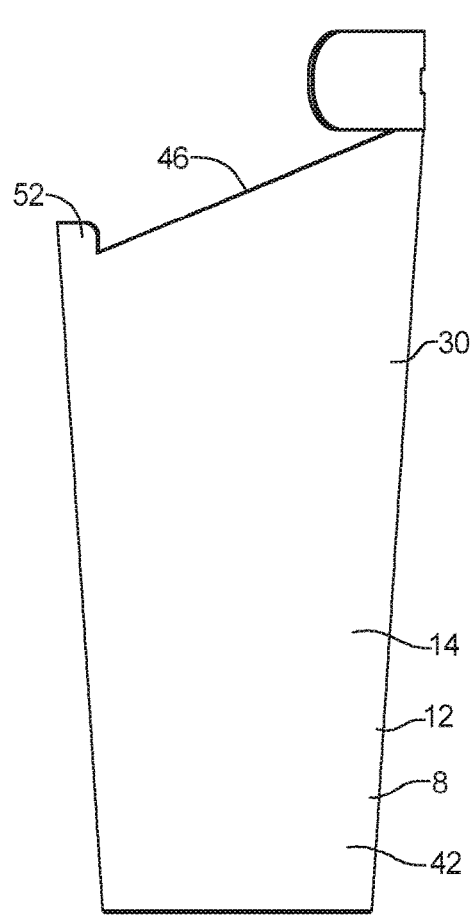
FIGS. 23, 24 and 25 represent right side, rear and bottom views of the medical device holder shown in FIG. 20.
Figure 24:
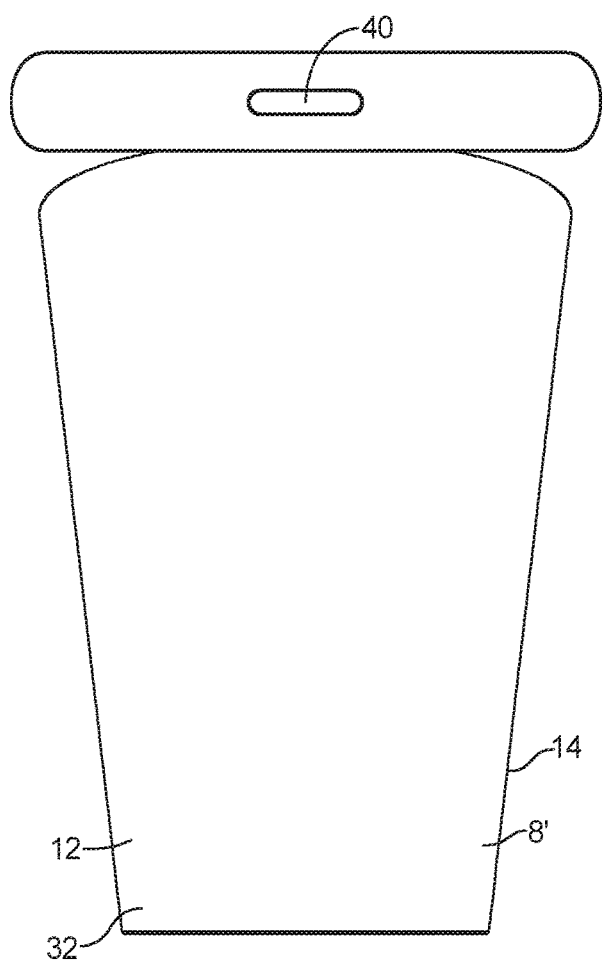
Figure 25:
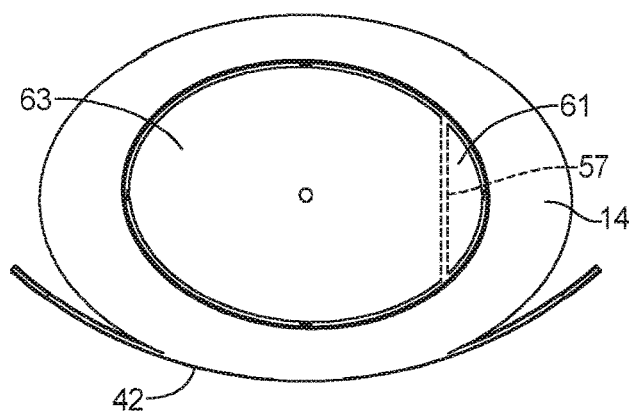
Figure 26:
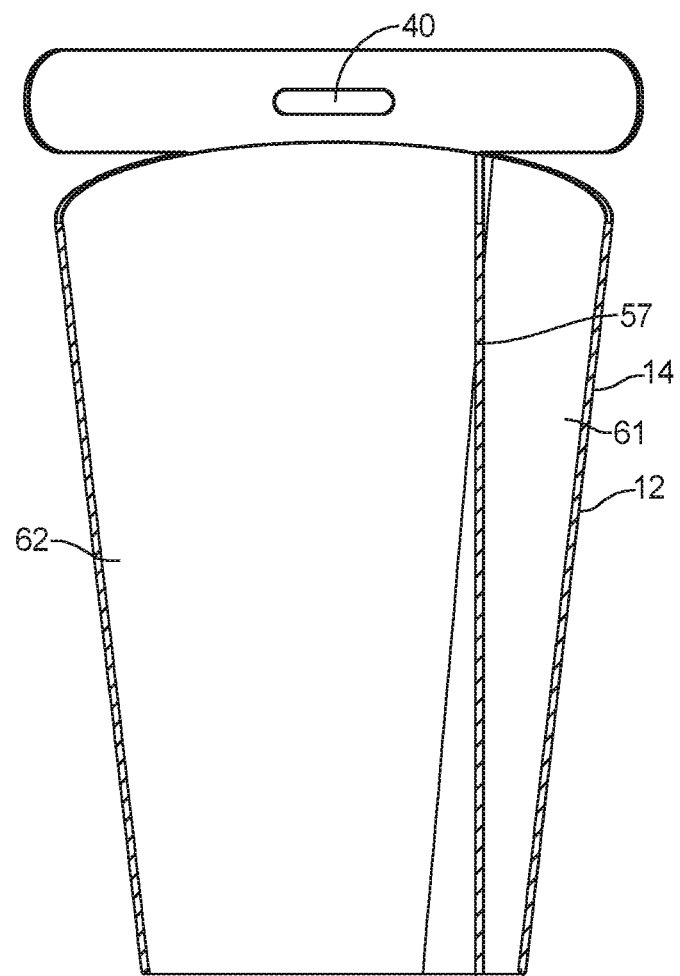
FIGS. 26 and 27 represent top and sectional views of the medical device holder shown in FIG. 25.
Figure 27:
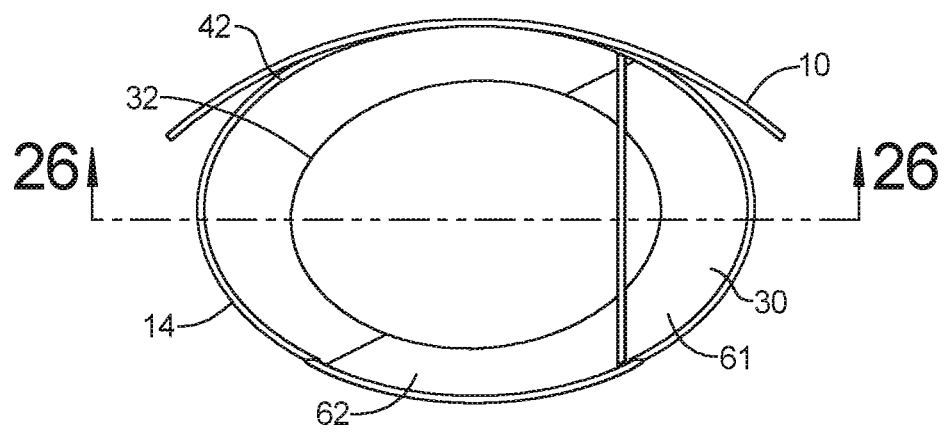

As shown in FIG. 23, the attachment mechanism is in the form of aperture 40 extending through a middle portion of support surface member 10, which may be utilized to as will be discussed in more detail below. Also shown is the curved back portion 42 that takes the general form of a rectangle component that couples to the curved surface of the sidewall 14 of the main body 12. The opening 21 defines a peripheral edge 44 that is segmented in three defined portions, the first and third portions 46 and 48 couple to the curved rectangular back portion 42. Coupled to a second end 50 of the first and third portions 46 and 48 is the second protrusion which defines a protruding lip 52, which along with the first and third portions define a scalloped surface which is configures to reduce the tendency of the medical instrument from rotating along the peripheral edge. Disposed within the cavity as a flange 57 that segments the body into a pair of cavities 61 and 63.

FIGS. 28a-28g represent views of an alternate medical device holder according to the present teachings. With initial reference to FIG. 28a, a medical instrument holder assembly 8''' is shown including a curved support surface member 10, and a main body 12 of the present invention mounted thereto. The curved support surface member 10 can be attached to the housing with a plurality of snap features. At least one sidewall 14 defining an elongated instrument housing 20 having an opening 21 through which a medical instrument (not shown) may be inserted. Preferably, instrument housing 20 is constructed of a semi-rigid plastic. However, housing 20 may alternatively be constructed from fully rigid or flexible materials, or a combination thereof. In this embodiment, main body 12 includes an upper portion 30 that tapers to an end portion 32.

The upper portion 30 and end portion 32 both include generally cylindrical diameters, wherein the diameter of upper portion 30 is larger than the diameter of end portion 32, forming an edge 34 there between. Extending through upper portion 30 is a locking slot or notch 40 which may be utilized to secure the medical device holder to the environment, such as a surgical drape as will be discussed in more detail below.

Figure 28A:
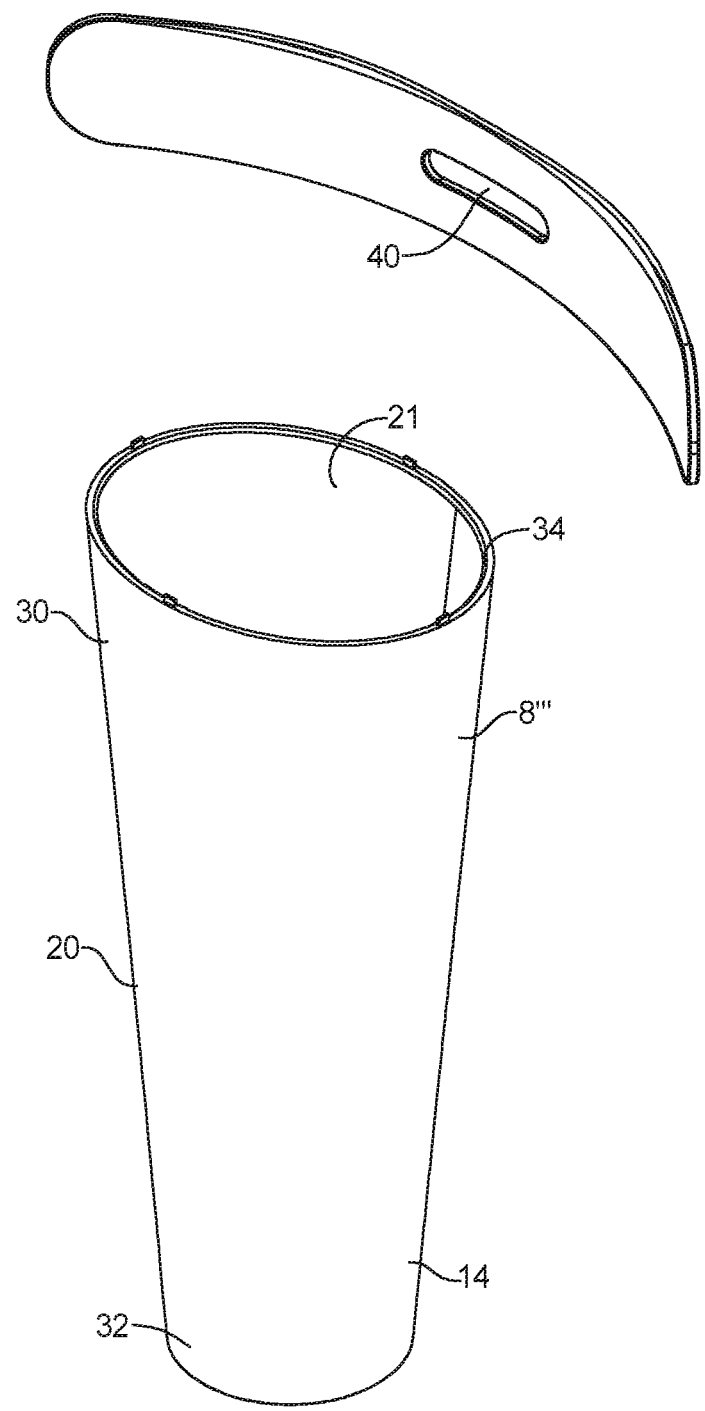
FIGS. 28a-28g represent views of an alternate medical device holder according to the present teachings.
Figure 28C:
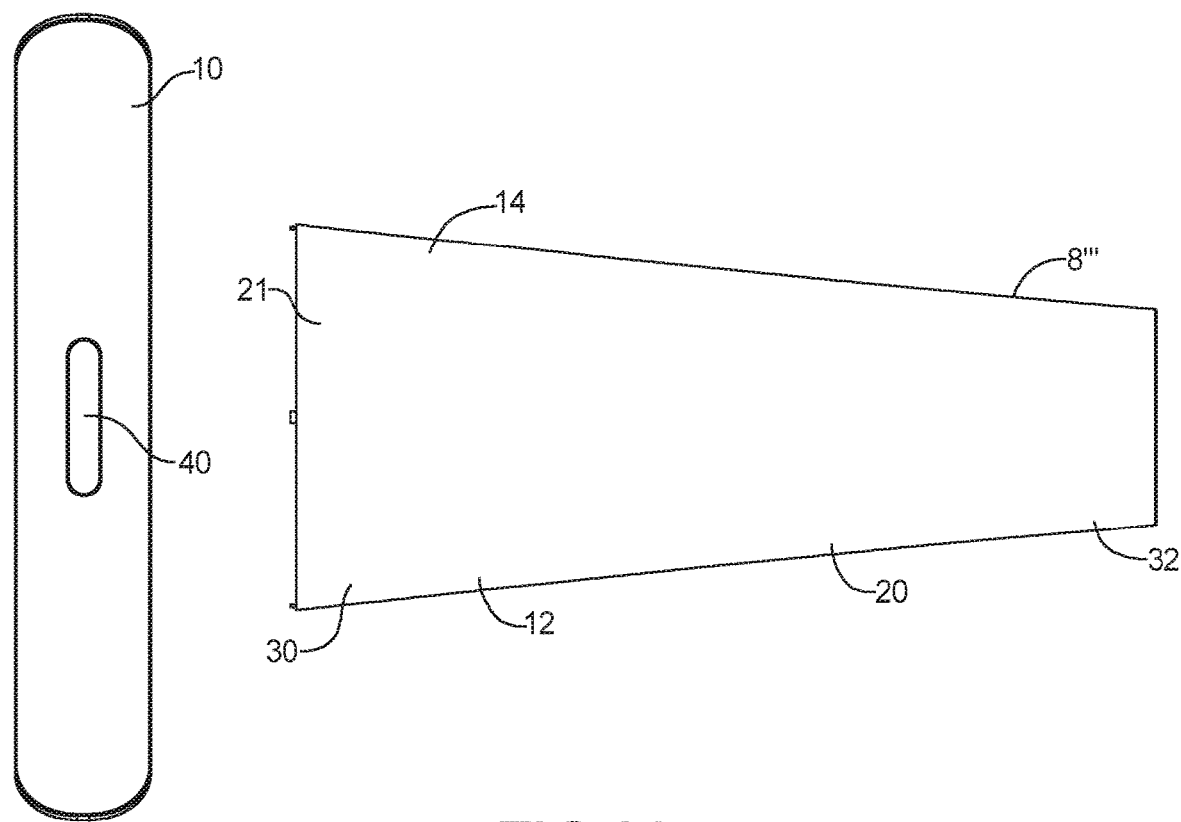
Figure 28B:
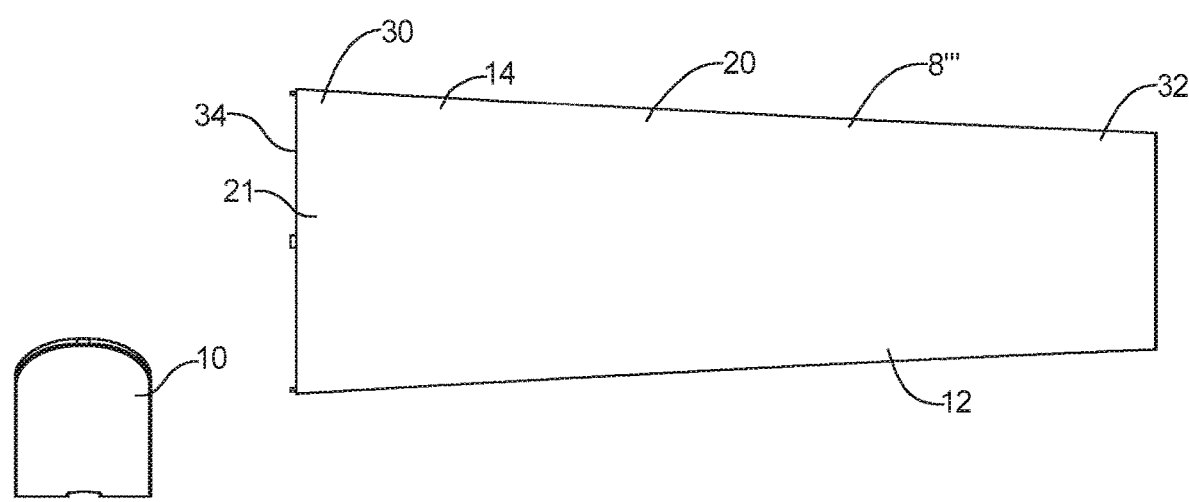
Figure 28D:
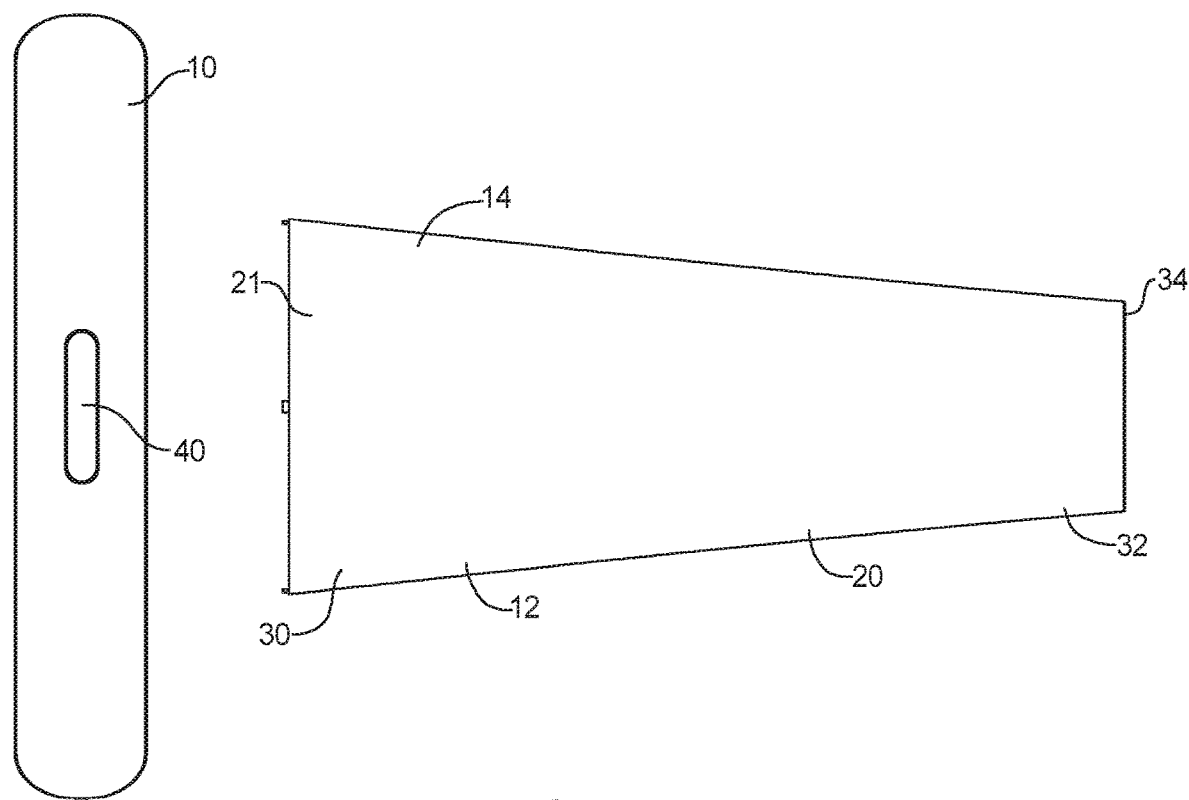
Figure 28E:
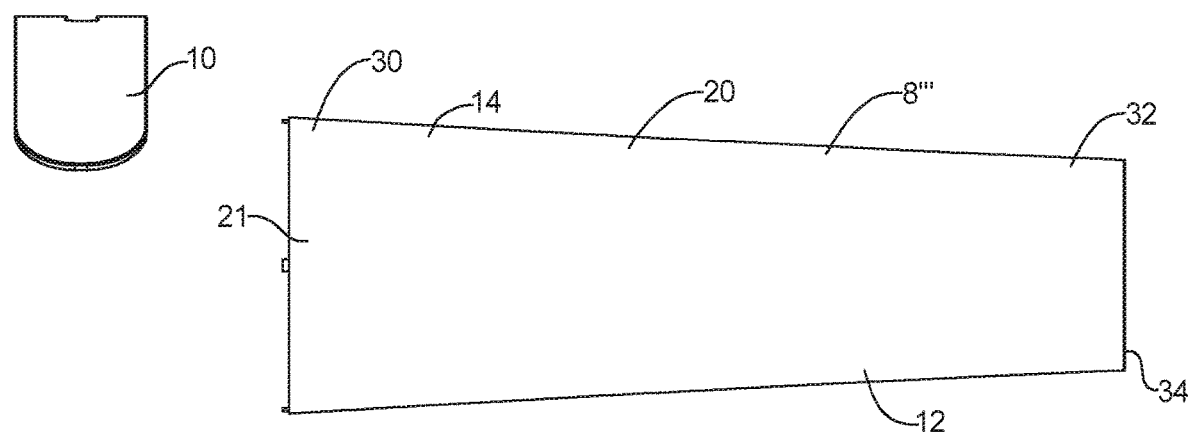
Figure 28F:
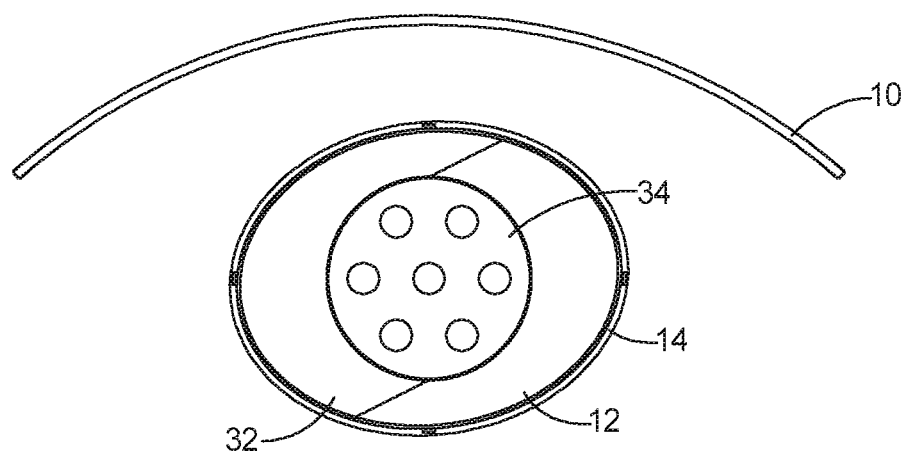
Figure 28G:
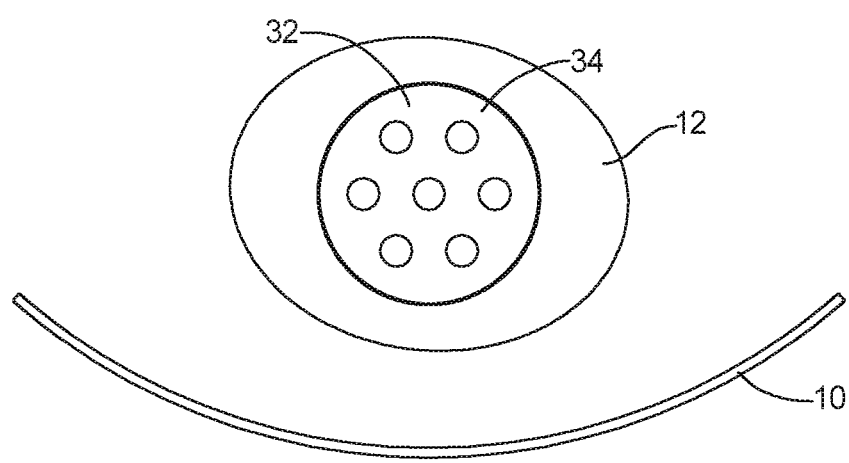
Figure 30:
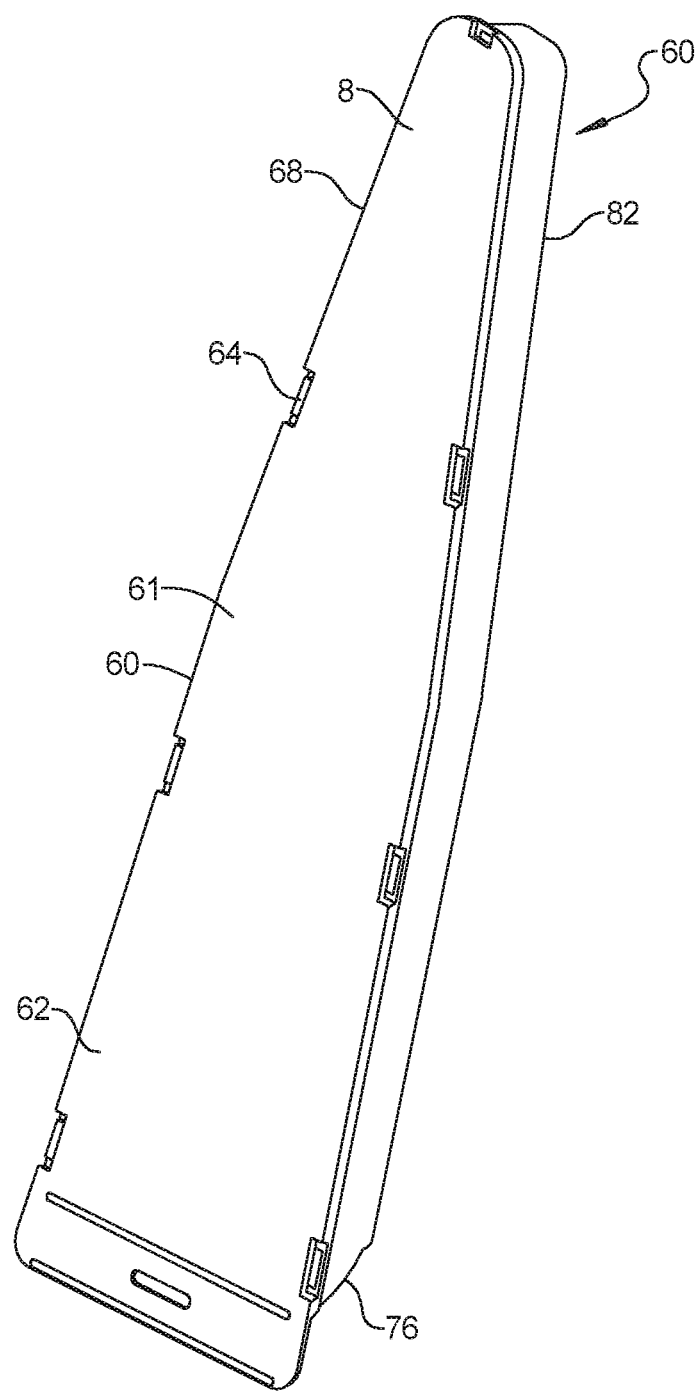
FIG. 30 represents a rear perspective view of a medical device holder shown in FIGS. 29a-29g.
Figure 31:
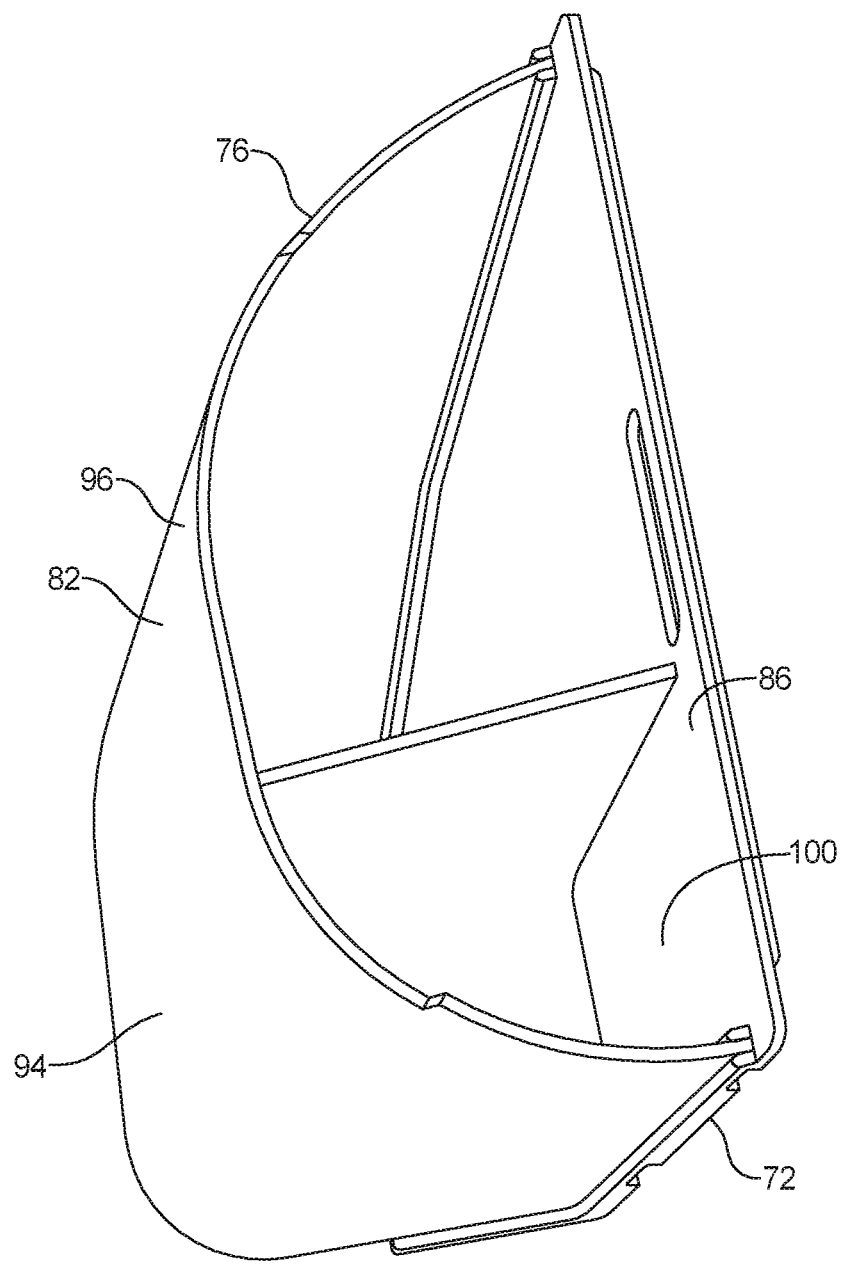
FIG. 31 represents a top perspective view of the medical device holder shown in FIGS. 29a-30.

As shown in FIG. 28d, the attachment mechanism is in the form of aperture 40 extending through a middle portion of support surface member 10, which may be utilized to as will be discussed in more detail below. Also shown is the curved back portion 42 that takes the general form of a rectangle component that couples to the curved surface of the sidewall 14 of the main body 12. The opening 21 defines a peripheral edge 44 which is segmented in three defined portions, the first and third portions 46 and 48 couple to the curved rectangular back portion 42. Coupled to a second end 50 of the first and third portions 46 and 48 is the second protrusion which defines a protruding lip 52, which along with the first and third portions define a scalloped surface which is configures to reduce the tendency of the medical instrument from rotating along the peripheral edge. Disposed within the cavity as a flange 57 that segments the body into a pair of cavities 61 and 63.

FIGS. 29a-31 represent an alternate holster according to the present teachings. The first planar support member 8 is coupled to the second concave support member 60. The first support member has a generally rectangular support member 62 that defines a coupling slot 64. The planar support has a first tapered portion 61 extending from the rectangular end 62 to a second tapered portion 68. The width of the second portion reduces from the width of the first tapered portion to a curved end or nose portion 70.

The first planar periphery 72 defines a plurality of flange capturing slots. Optionally, a living hinge can be defied between the first planar support member 68 and the concave support member 70. The second support member 70 is configured to be mated with the first support member 72, and has a first end 74 defining an angled scalloped surface 76. The scalloped surface 76 defines at least one notch or bearing surface 78 configured to support a medical device disposed within the hold.

The second support member 70 has a first tapered portion 80 that generally corresponds to the top of the first tapered portion 76 of the first member 68. The first tapered portion has a first and second curved sidewalls 82 which intersect at a triangular planar portion 84. Disposed within a concave surface 86 of the first portion 80 is an L-shaped member 86. The L-shaped member defines a first longitudinal cavity 88 when the first member 68 is coupled to the second member 70. The L-shaped member 86 is positioned so it has a first end 90 that generally aligns with the first end of the first portion 80. In this regard, the first end of the first portion and first end 90 define an angular plane 92.

Coupled to the first portion 80 is a second tapered portion 92. The second tapered portion has a changing width, between the width of the first portion to a width define by the end or nose of the first support member 8. The second portion 92 has a pair of curved sidewalls 94 and 96, which intersect along a central line.

When coupled together, the first and second support members 68, 70 form the first and second medical instrument support chambers. The second chamber 100 being generally L-shaped. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Further, while one preferred embodiment illustrates a storage device primarily designed to work with a cauterizing instrument, a family of storage devices of varying sizes can be designed to accommodate different medical instruments, and each member of the family of devices may have a different method of temporarily securing the medical instrument in the holder between uses. In addition, the storage device of the present invention can be incorporated into the packaging of a medical device or instrument, thus allowing for a more economical way to package and store the device. Finally, the particular shape and construction of the housing could vary. For instance, the housing could have any uniform size/geometry, including circular, oval, polygonal or the like cross-sections. In any case, the invention is only intended to be limited by the scope of the following claims. The device can be made of varying polymer materials, such as Nylon or Polypropylene. For example, the device can be formed of a material having a specific gravity of 1.25, a mass flow rate ar 230 deg C. of 15 g/10 min a tensile strength of 4250 psi and a flexural modulus of about 535 ksi and a hardness of 75 D.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical device holder comprising:
a first generally planar member having a first peripheral edge, the first generally planar member having a plurality of first coupling members disposed along the first peripheral edge and having a first end with a first width and a second end having a second width less than the first end, and the width of the first generally planar member tapering from the first end having the first width towards the second end having the second width; and
a housing having a concave member defining a second peripheral edge, the second peripheral edge having a plurality of second coupling members configured to interface with the first coupling members, and when the second coupling members and the first coupling members interface the concave member defines a first L-shaped chamber having a tapered configuration at the second end, a second chamber separate from the first L-shaped chamber, a first opening that is in communication with the first L-shaped chamber and having a third width, and a second opening that is in communication with the second chamber and having a fourth width, wherein the third and fourth widths extend along the first width and together define a total width that is substantially equal to the first width.

2. The medical device holder of claim 1 wherein the first generally planar member defines a coupling mechanism for securing the medical device holder to an external surface.

3. The medical device holder of claim 1 further comprising an L-shaped flange disposed on the concave member.

4. The medical device holder of claim 1 further comprising an L-shaped flange disposed on the first generally planar member.

5. The medical device holder of claim 1 wherein the first coupling member comprises a defined slot.

6. The medical device holder of claim 1 wherein the second coupling member is a deformable flange.

7. The medical device holder of claim 1 wherein the first generally planar member and the housing each comprise one or more polymers, each polymer of the one or more polymers having a melting point greater than about 212 degrees F.

8. The medical device holder of claim 7 wherein the one or more polymers include at least one of Nylon and polypropylene.

9. A medical device holder comprising:
a first generally planar member having a first end with a first width and a second end having a second width less than the first end, wherein the width of the first generally planar member tapers from the first end having the first width towards the second end having the second width, having a first peripheral edge, and having a plurality of first coupling members disposed along the first peripheral edge; and
a housing having a concave member defining a second peripheral edge configured to mate with the first peripheral edge, the second peripheral edge having a plurality of second coupling members configured to interface with the first coupling members, the concave member having an L-shaped member and when the second coupling members and the first coupling members interface the L-shaped member defines a first L-shaped chamber having a tapered configuration at the second end between the L-shaped member and the concave member and a second chamber separate from the first L-shaped chamber, and when the second coupling members and the first coupling members interface the concave member also defines a first opening that is in communication with the first L-shaped chamber and having a third width, and a second opening that is in communication with the second chamber and having a fourth width, wherein the third and fourth widths extend along the first width and together define a total width that is substantially equal to the first width, and wherein the first peripheral edge and the second peripheral edge are also joined by a living hinge.

10. The medical device holder of claim 9 wherein the first coupling members comprise a plurality of slots defined in the first generally planar member.

11. The medical device holder of claim 9 wherein the second coupling members comprise a plurality of deformable flanges.

12. The medical device holder of claim 9 wherein the housing and the first generally planar member are monolithic in nature and made by injection molding.

13. The medical device holder of claim 9 wherein the L-shaped member is disposed between the first generally planar member and the concave member.

14. A medical device holder comprising:
   a housing having a concave member defining an edge having a plurality of housing coupling members, the concave member having an L-shaped member which defines a first L-shaped chamber between the first L-shaped member and the concave member and a second chamber separate from the first L-shaped chamber; and
   a generally planar member having a first end with a first width and a second end having a second width less than the first end, wherein the width of the first generally planar member tapers from the first end having the first width towards the second end having the second width, having a planar member peripheral edge, and having a plurality of planar member coupling mechanisms disposed along the planar member peripheral edge, the planar member coupling mechanism configured to couple to the housing coupling member, and when the planar member coupling mechanism is coupled to the housing coupling member the concave member defines a first opening that is in communication with the L-shaped chamber and having a third width, and a second opening that is in communication with the second chamber and having a fourth width, the third and fourth widths extending along the first width and together defining a total width that is substantially equal to the first width, and the L-shaped chamber having a tapered configuration at the second end, and the generally planar member also having one or more scraping surfaces molded or glued on to a surface of the generally planar member.

15. The medical device holder of claim 14 wherein the generally planar member defines a coupling slot.

16. The medical device holder of claim 14 wherein the housing is coupled to the generally planar member with a living hinge.

17. The medical device holder of claim 14 wherein the housing being made by injection molding.

18. The medical device holder of claim 14 wherein the generally planar member comprises a mounting channel component.

19. The medical device holder of claim 14 wherein the generally planar member comprises a flange that forms the planar member coupling mechanisms.

20. The medical device holder of claim 18 wherein the mounting channel has a channel configuration that is rectangular in nature.

21. The medical device holder of claim 14 wherein the planar member coupling mechanism comprises a channel that defines a plurality of slots.

* * * * *